(12) United States Patent
Tsuchida et al.

(10) Patent No.: US 6,558,700 B1
(45) Date of Patent: May 6, 2003

(54) MULTIPLE-UNIT SUSTAINED RELEASE TABLETS

(75) Inventors: Kazutaka Tsuchida, Tokyo (JP); Shinji Aoki, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/673,398

(22) PCT Filed: Aug. 7, 1998

(86) PCT No.: PCT/JP98/03537

§ 371 (c)(1),
(2), (4) Date: Oct. 17, 2000

(87) PCT Pub. No.: WO99/53905

PCT Pub. Date: Oct. 28, 1999

(30) Foreign Application Priority Data

Apr. 17, 1998 (JP) .......................................... 10-107349

(51) Int. Cl.⁷ ................................................. A61K 9/26
(52) U.S. Cl. ...................... 424/469; 424/400; 424/464; 424/468; 424/470; 424/472; 424/474
(58) Field of Search ................................ 424/400, 464, 424/468, 469, 470, 474, 489, 490

(56) References Cited

U.S. PATENT DOCUMENTS

| | | | |
|---|---|---|---|
| 4,710,384 A | 12/1987 | Rotman et al. | 424/465 |
| 5,246,714 A | * 9/1993 | Dahlinder et al. | 424/497 |
| 5,624,683 A | * 4/1997 | Andoh et al. | 424/470 |

FOREIGN PATENT DOCUMENTS

| | | | |
|---|---|---|---|
| JP | 7-53361 | 2/1995 | |
| JP | 7-53365 | 2/1995 | |
| JP | 7-316042 | 12/1995 | ............ A61K/9/22 |
| JP | 8-40905 | 2/1996 | |
| JP | 8-17983 | 7/1996 | |
| JP | 2601660 | 1/1997 | ............ A61K/9/22 |
| JP | 9-169645 | 6/1997 | |
| JP | 10-218761 | 8/1998 | |
| WO | 95/10264 | 4/1995 | |

OTHER PUBLICATIONS

International Search Report.

* cited by examiner

Primary Examiner—Thurman K. Page
Assistant Examiner—Charesse Evans
(74) Attorney, Agent, or Firm—Sughrue Mion, PLLC

(57) ABSTRACT

A multiple-unit sustained release tablet characterized by consisiting of a granular part and a powdery part, each granule comprising a matrix composed of a water-insoluble polymer and an active ingredient.

Another tablet characterized in that each granule is coated with a release-controlling film.

The object of the present invention is to provide a multiple-unit sustained release tablet showing little change in dissolution speed caused by the compression in the tableting step.

8 Claims, 6 Drawing Sheets

Comparative Example 1

Comparative Example 2

MULTIPLE-UNIT SUSTAINED RELEASE TABLETS

TECHNICAL FIELD

This invention relates to a multiple-unit sustained release tablet comprising a granular part and a powdery part.

BACKGROUND ART

Pharmaceutical preparations for controlling a dissolution rate of an active ingredient may be classified into a single-unit pharmaceutical preparation and a multiple-unit pharmaceutical preparation. The single-unit pharmaceutical preparation is mainly in the form of tablets, while the multiple-unit one is mainly in the form of capsules or granules. The multiple-unit pharmaceutical preparation is superior to the single-unit one in the following characteristics: (1) less change in absorption of an active ingredient, (2) easier reproducibility of dissolution, and (3) being applicable to two or more active ingredients. Due to these excellent features, the multiple-unit pharmaceutical preparation is desirable as a sustained release preparation. The multiple-unit pharmaceutical preparation is desirably in the form of tablets rather than capsules or granules so that it may be taken more easily.

However, the conventional multiple-unit sustained release tablet is prepared by coating core particles with a drug layer, coating the surface of said coated particles with a release-controlling agent to form sustained release granules, blending said granules with a powdery part and then compressing to tablets. A sustained release film of the granules may often be broken during compression to tablets, resulting in difficulty in controlling dissolution of the drug. For coping with these problems, there have been proposed multiple-unit tablets, which comprises a granule of an indefinite form and a powdery part, said granule being composed of an uncoated granule containing low-melting fats and oils and an active ingredient, and a release-controlling film (JP-A-7-316042), or sustained release compression tablets prepared by compressing numerous microcapsules composed of fine particles of an active ingredient, said active ingredient being coated with a sustained release polymer composition, wherein said microcapsules have non-uniform particle diameters within the range of from about 5 $\mu$ to about 400 $\mu$ and can be immediately disintegrated in an aqueous solution to disperse into individual microcapsules (Japanese Patent No. 2601660). However, sustained release granules according to the prior art having an indefinite and unequal shape would make it difficult to apply a uniform coating film and to prepare sustained release tablets with a stable dissolution rate.

The object of the invention is to provide multiple-unit sustained release tablets with little change in dissolution rate caused by compression during tableting step.

DISCLOSURE OF THE INVENTION

We have found that the above problems can be dissolved by using a granule comprising a matrix composed of a water-insoluble polymer and an active ingredient (hereinafter referred to as a matrix granule) or said matrix granule further coated with a release-controlling film (hereinafter referred to as a coated granule), upon which the present invention has been completed.

More specifically, the present invention includes the following inventions:

(1) A multiple-unit sustained release tablet characterized by consisting of a granular part and a powdery part, each granule in the granular part comprising a matrix composed of a water-insoluble polymer and an active ingredient.

(2) The multiple-unit sustained release tablet as described in the item (1), wherein said granule comprises a core particle and a matrix layer composed of a water-insoluble polymer and an active ingredient for coating said core particle.

(3) The multiple-unit sustained release tablet as described in the item (1) or (2), wherein a weight ratio of said water-insoluble polymer to said active ingredient is 0.7:1–3:1.

(4) The multiple-unit sustained release tablet as described in any of the items (1)–(3), wherein said water-insoluble polymer is ethyl cellulose.

(5) The multiple-unit sustained release tablet as described in the item (4), wherein said ethyl cellulose has a viscosity of not less than 15 cps at 25° C. when dissolved at 5% by weight in a mixed solution of toluene and ethanol (8:2 w/w).

(6) The multiple-unit sustained release tablet as described in any of the items (1)–(5), wherein said granule is coated with a release-controlling film.

(7) The multiple-unit sustained release tablet as described in the item (6), wherein said release-controlling film is a water-insoluble polymer.

(8) The multiple-unit sustained release tablet as described in the item (6) or (7), wherein said water-insoluble polymer is ethyl cellulose.

(9) The multiple-unit sustained release tablet as described in any of the items (6)–(8), wherein said granule has a granule strength of not less than 3,000 g/mm$^2$ in the state not coated with said release-controlling film.

The water-insoluble polymer as used herein means a water-insoluble polymer used in the pharmaceutical field as a sustained release coating agent, an enteric coating agent, a gastric coating agent, etc., which may include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethyl-cellulose, cellulose acetate phthalate, methacrylic acid copolymer L, methacrylic acid copolymer LD, methacrylic acid copolymer S, aminoalkyl methacrylate copolymer E, polyvinyl acetal diethylaminoacetate, etc. Of these polymers, ethyl cellulose may be most preferable.

Preferably, the type, degree of substitution and molecular weight of the water-insoluble polymers should be chosen for their proper use, depending on solubility of the active ingredient in water or an alcohol, the desired sustained release level and the like. These water-insoluble polymers may be used either alone or in combination. There may be further incorporated a hydrogenated oil, stearic acid, cetanol, etc. as a coating auxiliary agent, and a middle-chain triglyceride, triacetin, triethyl citrate, cetanol, etc. as a plasticizer.

The ethyl cellulose used herein preferably has an ethoxyl content of 43–50% (substitution degree of 2.2–2.6). In order to carry out the invention, ethyl cellulose has a viscosity of not less than 15 cps, preferably not less than 20 cps, more preferably 20–50 cps, at 25° C. when dissolved at 5% by weight in a mixed solution of toluene and ethanol (8:2 w/w).

A solvent for the water-insoluble polymer may vary depending on the type of the polymer. In general, a mixture of water and a lower alcohol or a lower alcohol is preferable.

In case of ethyl cellulose, a 60% or more aqueous ethanol solution is preferable. It is essential that the water-insoluble polymer be dissolved in such a solvent and that an active ingredient be dissolved or uniformly dispersed in the water-insoluble polymer solution. Where the active ingredient is of a dispersed form, it is effective to maintain an average particle diameter below 20 µm for improving adhesion to a core particle and securing uniformity, and to perform a sufficient stirring for establishing uniformity.

The present invention may be applied to various active ingredients including water-soluble drugs by varying the type of water-insoluble polymers or blending ratio thereof or by additional coating of the matrix granule with a release-controlling film. Accordingly, the kind of the active ingredient to be used in this invention is not particularly restricted. The active ingredients which may be used in this invention are exemplified as follows: Diprophylline, dextromethorphan hydrobromide, phenylpropanolamine hydrochloride, belladonna (total) alkaloids, acetaminophen, theophylline, sodium salicylate, aspirin, ibuprofen, noscapine, dl-methylephedrine hydrochloride, dihydrocodeine phosphate, ethenzamide, bromhexine hydrochloride, d-chlorpheniramine maleate, aminophylline, proxyphylline, caffeine, etc. These active ingredients may be used in admixture with two or more thereof.

According to the invention, it is feasible to freely control dissolution rate of the active ingredient, considering its solubility in water, according to the type of the water-insoluble polymer forming the matrix granule, the blending ratio of the water-insoluble polymer to the active ingredient and others. It is also feasible to control the dissolution rate, changing the composition of the solvent for dissolving the water-insoluble polymer. Blending ratio of the water-insoluble polymer to the active ingredient, both forming the matrix granule, may be properly selected in such a range that may control dissolution of the active ingredient, and is usually 0.7:1–3:1, preferably 0.75:1–1.25:1 in terms of weight ratio. In the production according to the invention, an amount of the water-insoluble polymer to be incorporated in the matrix granule may be preferably three times or less that of the active ingredient. However, if it is difficult to ensure the desired dissolution rate of the active ingredient by using said amount, it will be more efficient to control dissolution rate of the active ingredient by coating the matrix granule with a release-controlling film. In that case, a granule strength of the matrix granule is kept preferably not less than 3,000 g/mm², more preferably not less than 3,500 g/mm². This will make the coated granule hardly broken during mixing with the powdery part and compressing to tablets. Thus, it becomes feasible to lessen a change in the dissolution rate of the coated granules.

Granule strength may be controlled by choosing the type, degree of substitution and molecular weight of the water-insoluble polymer for intended use and adequately selecting a blending ratio of the water-insoluble polymer to the active ingredient.

Embodiments of the present invention are illustrated below, but the invention is not limited thereto.

If dissolution of an active ingredient contained in the matrix granule is to be controlled for a short period of time, or if dissolution of an active ingredient which is slightly soluble in water or an alcohol is to be controlled, the matrix granule may be used as such because desired dissolution control is easily accomplished without coating it with a release-controlling film. On the other hand, if dissolution of the active ingredient contained in the matrix granule is to be controlled over a long period of time, it is required to coat the granule with a release-controlling film in an amount suitable for the desired dissolution rate. The release-controlling film which may be used herein may include water-insoluble polymers as exemplified above, ethyl cellulose being preferable.

A core particle, which may be optionally used for the matrix granule, may be a spherical granule of a crystalline cellulose or a spherical granule of a lactose crystalline cellulose (For example, Celphere; manufactured by Asahi Chemical Industry Co., Ltd., Nonpareil; manufactured by Freund Industrial Co., Ltd.). An average particle diameter of the core particle ranges preferably between 100–1000 µm.

The method of granulating the matrix granule using the core particle includes those using a compound coater, a rolling fluidized coater, a fluidized bed coater, etc. The granulation method without using the core granule includes wet cylindrical granulation using a kneader or a granulator, and heat-molten, agitating granulation using LEADEGE Mixer, High Speed Mixer, etc. For coating the matrix granule with a release-controlling film, an ordinary fluidized bed coater or a ventilation pan coater, etc. can be used. Subsequent curing procedure, if necessary, may also be effective. The curing procedure is preferably carried out at 70° C. or higher.

The powdery part as used herein means the part, which comprises other components than the active ingredient (drug) and, if necessary, the active ingredients that are the same as and/or different from the active ingredient contained in the matrix granule, and which may disintegrate immediately after administration to release the granular part and simultaneously to initiate dissolution of the active ingredient (drug), if contained. The other components than the active ingredient (drug) as mentioned above may be excipients, disintegrating agents, lubricants, etc. conventionally used in tablets, for example, microcrystalline cellulose, light silicic anhydride, low substututed hydroxypropyl cellulose, hydroxypropyl cellulose, lactose, corn starch, magnesium stearate and the like, which are used in admixture therewith.

The tablet according to the invention preferably has a blending ratio by weight of the granular part to the powdery part of 1:0.5 or more. If the ratio of the powdery part is less than 0.5, a rapid disintegration into sub-units may be prevented or a poor moldability to tablet may be caused owing to mutual contact of the granular parts. An amount of the powdery part to be used has no upper limit set. No particular limitation is set on mixing of the granular part with the powdery part and compressing to tablets, which may be carried out according to a conventional method using any ordinary mixer or tablet machine. The present invention can provide sustained release tablets with little change in dissolution rate, even if a higher compression pressure has been applied. Compression pressure is usually not less than 0.6 t, preferably 1.0–2.5 t.

BEST MODE FOR CARRYING OUT THE INVENTION

Figure 1:
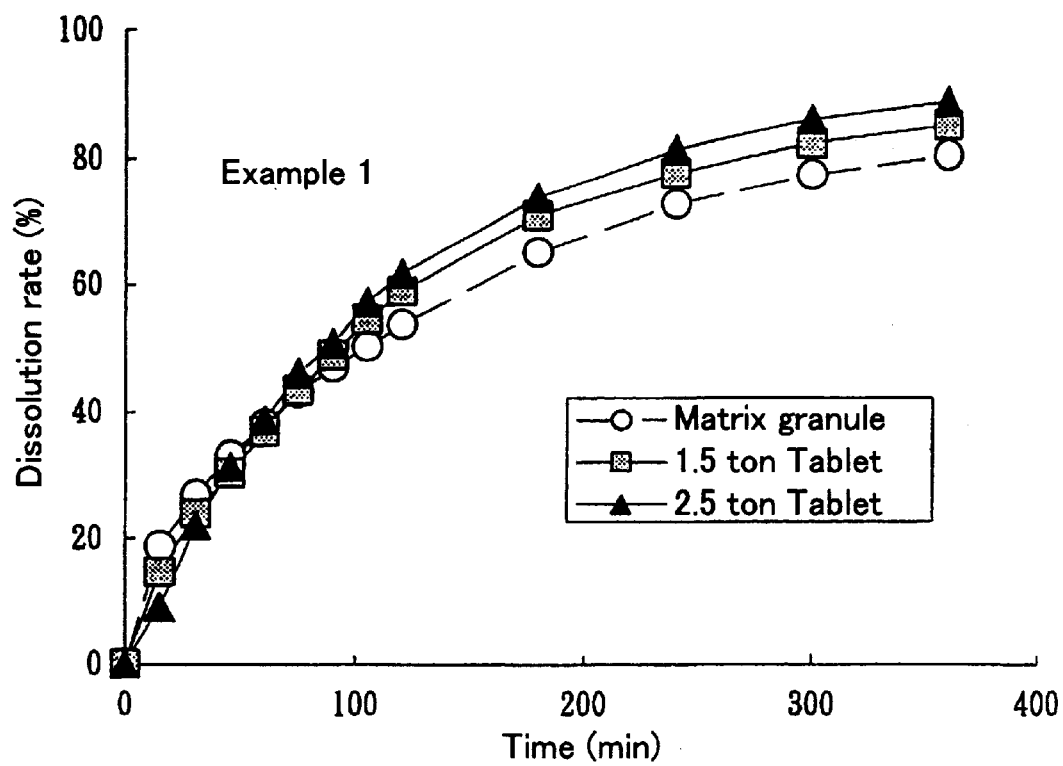
FIG. 1 shows the results from dissolution test of sustained release granules and tablets prepared in Example 1.

The present invention will be illustrated in more detail by way of the following Examples and Test Examples.

Example 1

In 4000 g of 95% ethanol was dispersed 500 g of diprophylline and the dispersion was ground by means of a colloid mill to regulate an average diameter to not more than 20 $\mu$m. Then, dissolved therein was 500 g of ethyl cellulose (having a viscosity of 20 cps at 25° C. when dissolved at 5% by weight in a toluene—ethanol mixed solvent (8:2 w/w); an ethoxyl content of 48.0–49.5% (degree of substitution of 2.41–2.51))(hereinafter referred to as "Ethyl Cellulose-20 cps"). The dispersion thus prepared was coated onto 1000 g of core particles (Celphere CP-305) by means of a bottom-spray type fluidized bed coater (manufactured by Powrex Co., Ltd., GPCG-1) to prepare a matrix granule (ethyl cellulose:diprophylline=1:1 (w/w)). One part of the matrix granule thus prepared was mixed with one part of the molding granule, which had been granulated by spraying 571.4 g of 7% hydroxypropyl cellulose/purified water onto 800 g of the powdery part obtained by mixing lactose and corn starch at 7:3 by means of a fluidized bed granulator (Freund Industrial Co., Ltd., type FLO-1). Magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Example 2

In 9000 g of 95% ethanol were dissolved 500 g of dextromethorphan hydrobromide and 500 g of ethyl cellulose (having a viscosity of 45 cps at 25° C. when dissolved at 5% by weight in a toluene—ethanol mixed solvent (8:2 w/w); an ethoxyl content of 48.0–49.5% (degree of substitution of 2.41–2.51))(hereinafter referred to as "Ethyl Cellulose-45 cps"). The solution thus prepared was coated onto 1000 g of core particles (Celphere CP-305) by means of a bottom-spray type fluidized bed coater (manufactured by Powrex Co., Ltd., GPCG-1) to prepare a matrix granule (ethyl cellulose: dextromethorphan=1:1 (w/w)). One part of the matrix granule thus prepared was mixed with one part of the molding granules as granulated in the same manner as described in Example 1, magnesium stearate was added to the mixture at 0.2% and then the resulting mixture was compressed to As, tablets by means of a rotary tablet machine (under compression pressures of 1.5 t and 2.5 t) to prepare tablets, each tablet weighing 290 g.

Example 3

The matrix granule prepared in Example 2 was coated with the coating solution prepared by dissolving 300 g of Ethyl Cellulose-20 cps and 15 g of triethyl citrate in 7185 g of 76% ethanol by means of a bottom-spray type fluidized bed coater (manufactured by Powrex Co., Ltd., GPCG-1) to prepare a coated granule. One part of the coated granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Example 4

A matrix solution was prepared by dissolving 600 g of phenylpropanolamine hydrochloride and 600 g of Ethyl Cellulose-20 cps in 8800 g of 76% ethanol. The matrix solution thus prepared was coated onto 1000 g of core particles (Celphere CP-305) by means of a bottom-spray type fluidized bed coater (manufactured by Powrex Co., Ltd., GPCG-1) to prepare a matrix granule (ethyl cellulose:phenyl-propanolamine hydrochloride=1:1 (w/w)).

The coating solution was prepared by dissolving 440 g of Ethyl Cellulose-20 cps and 22 g of triethyl citrate in 10537 g of 76% ethanol. The coating solution thus prepared was coated onto the matrix granule by means of a bottom-spray type fluidized bed coater (manufactured by Powrex Co., Ltd., GPCG-1) to prepare a coated granule. One part of the coated granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Example 5

The coated granule having the composition as shown in Table 1 was prepared in the same manner as described in Example 4. One part of the coated granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Comparative Example 1

The matrix granule having the composition as shown in Table 2 was prepared in the same manner as described in Example 1. One part of the matrix granule thus prepared was admixed with one part of the molding granules as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Comparative Example 2

The matrix granule having the composition as shown in Table 2 was prepared in the same manner as described in Example 2. One part of the matrix granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Comparative Example 3

In 2188 g of purified water were dissolved 1129 g of phenylpropanolamine hydrochloride and 71 g of hydroxypropyl cellulose (having a hydroxypropoxyl content of 53.4–77.5%). The solution thus prepared was coated onto 1000 g of core particles (Celphere CP-305) by means of a bottom-spray type fluidized bed coater (manufactured by Powrex Co., Ltd., GPCG-1) to prepare an uncoated granule. Then, 440 g of Ethyl Cellulose-20 cps and 22 g of triethyl citrate were dissolved in 10531 g of 76% ethanol and the solution was coated onto the uncoated granule to prepare a coated granule. One part of the coated granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Comparative Example 4

The coated granule having the composition as shown in Table 2 was prepared in the same manner as described in Example 3. One part of the coated granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

Comparative Example 5

The coated granule having the composition as shown in Table 2 was prepared in the same manner as described in Example 3. One part of the coated granule thus prepared was admixed with one part of the molding granule as granulated in the same manner as described in Example 1, magnesium stearate was added to the mixture at 0.2% and then the resulting mixture was compressed to tablets by means of a rotary tablet machine (under compression pressures of 1.5 t and 2.5 t) to prepare tablets, each tablet weighing 290 g.

The formulation according to Examples and Comparative Examples is summarized in Tables 1 and 2.

TABLE 1

| (Unit: gram) | Example 1 | Example 2 | Example 3 | Example 4 | Example 5 |
|---|---|---|---|---|---|
| MATRIX GRANULE | | | | | |
| Celphere CP-305 | 1000 | 1000 | 1000 | 1000 | 1000 |
| Dipropylline | 500 | — | — | — | — |
| Dextromethorphan hydrobromide | — | 500 | 500 | — | — |
| Phenypropanolamine hydrochloride | — | — | — | 600 | 600 |
| Ethyl Cellulose - 20 cps | 500 | — | — | 600 | 450 |
| Ethyl Cellulose - 45 cps | — | 500 | 500 | — | — |
| 95% Ethanol | 4000 | 9000 | 9000 | 7040 | 6000 |
| Purified water | — | — | — | 1760 | 1500 |
| COATING FILM | | | | | |
| Ethyl Cellulose - 20 cps | — | — | 300 | 440 | 410 |
| Triethyl citrate | — | — | 15 | 22 | 20 |

TABLE 1-continued

| (Unit: gram) | Example 1 | Example 2 | Example 3 | Example 4 | Example 5 |
|---|---|---|---|---|---|
| 95% Ethanol | — | — | 5748 | 8430 | 7856 |
| Purified water | — | — | 1437 | 2107 | 1964 |

TABLE 2

| (Unit: gram) | Comparative Example 1 | Comparative Example 2 | Comparative Example 3 | Comparative Example 4 | Comparative Example 5 |
|---|---|---|---|---|---|
| MATRIX GRANULE | | | | | |
| Celphere CP-305 | 1000 | 1000 | 1000 | 1000 | 1000 |
| Dipropylline | 500 | — | — | — | — |
| Phenylpropanolamine hydrochloride | — | 600 | 1129 | 600 | 600 |
| Hydroxypropyl cellulose | — | — | 71 | — | — |
| Ethyl Cellulose - 7 cps | 500 | — | — | 600 | — |
| Ethyl Cellulose - 45 cps | — | 1800 | — | — | 300 |
| 95% Ethanol | 4000 | 33600 | — | 4800 | 5100 |
| Purified water | — | — | 2188 | — | — |
| COATING FILM | | | | | |
| Ethyl Cellulose - 20 cps | — | — | 440 | 440 | 380 |
| Triethyl citrate | — | — | 22 | 22 | 19 |
| 95% Ethanol | — | — | 8425 | 8425 | 7281 |
| Purified water | — | — | 2106 | 2106 | 1820 |

Test Example 1

The granules and tablets as prepared by Examples 1–5 and Comparative Examples 1–5 were subjected to dissolution test. The dissolution test was carried out in accordance with the Dissolution Test, Method 2 of the General Test and Assay as prescribed in the Pharmacopoeia of Japan.

Figure 2:
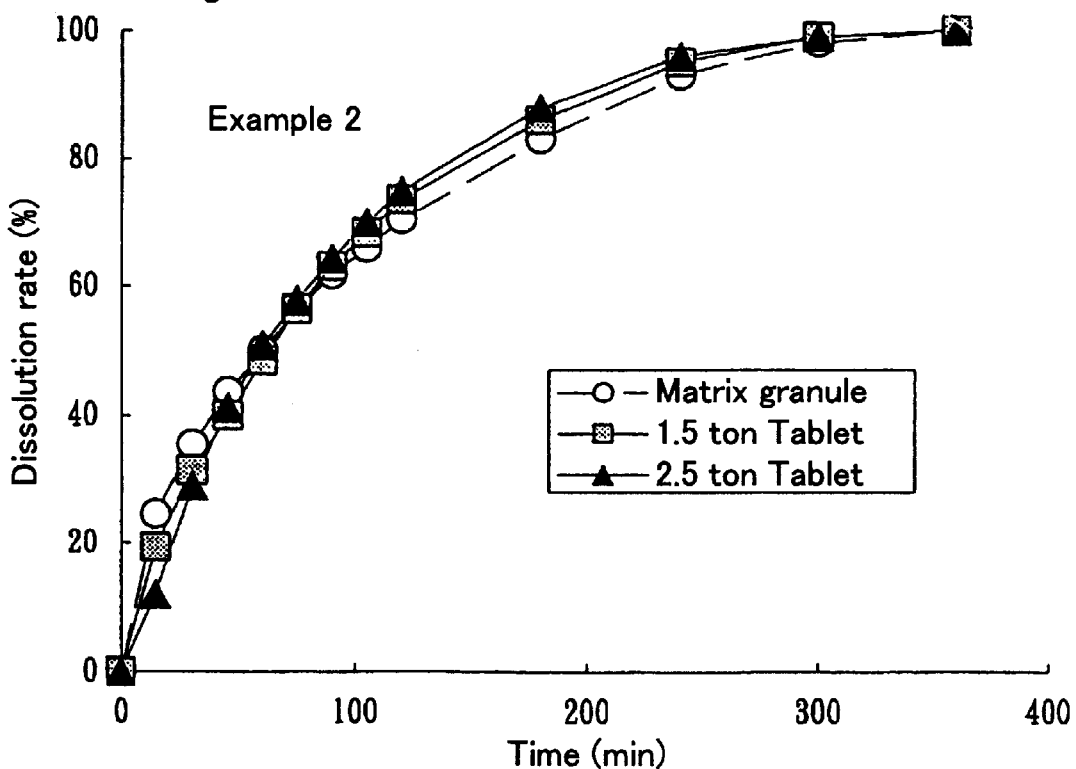
FIG. 2 shows the results from dissolution test of sustained release granules and tablets prepared in Example 2.
Figure 3:
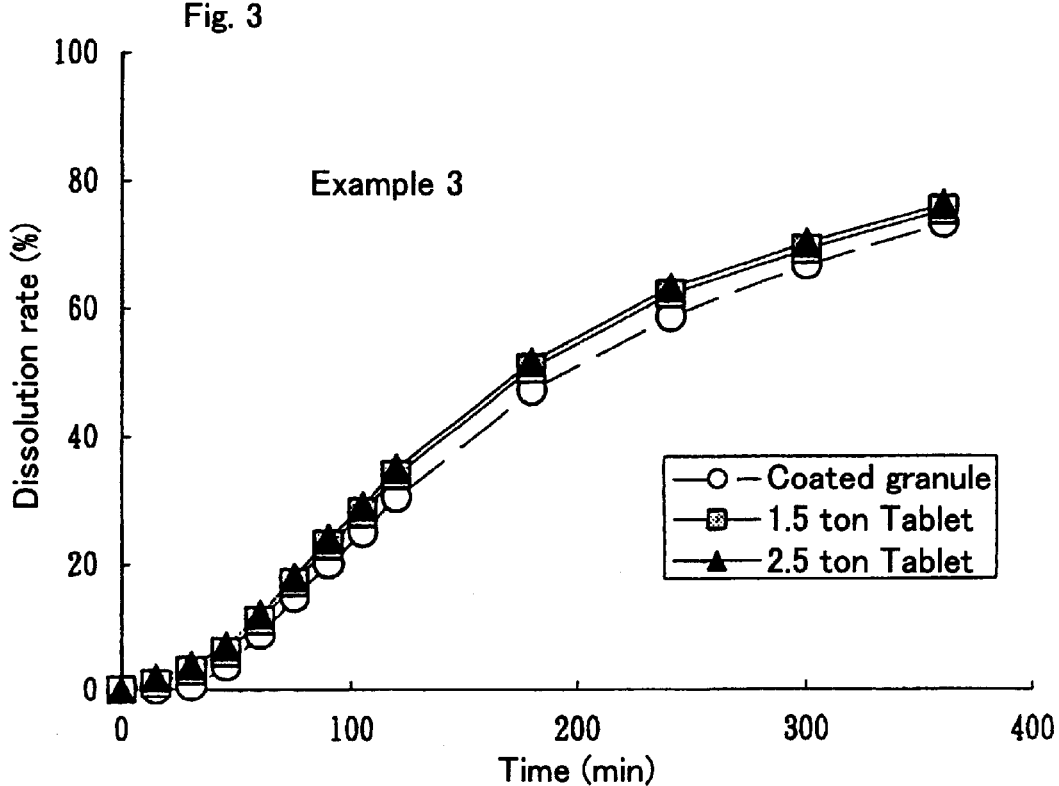
FIG. 3 shows the results from dissolution test of sustained release granules and tablets prepared in Example 3.
Figure 4:
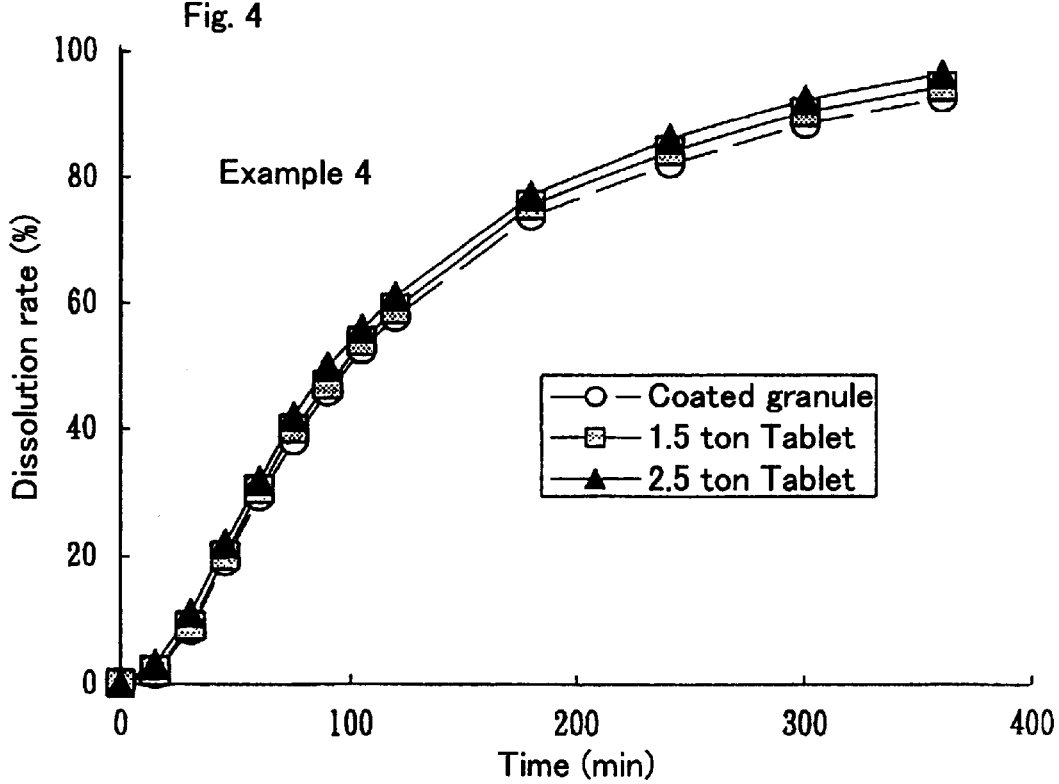
FIG. 4 shows the results from dissolution test of sustained release granules and tablets prepared in Example 4.
Figure 5:
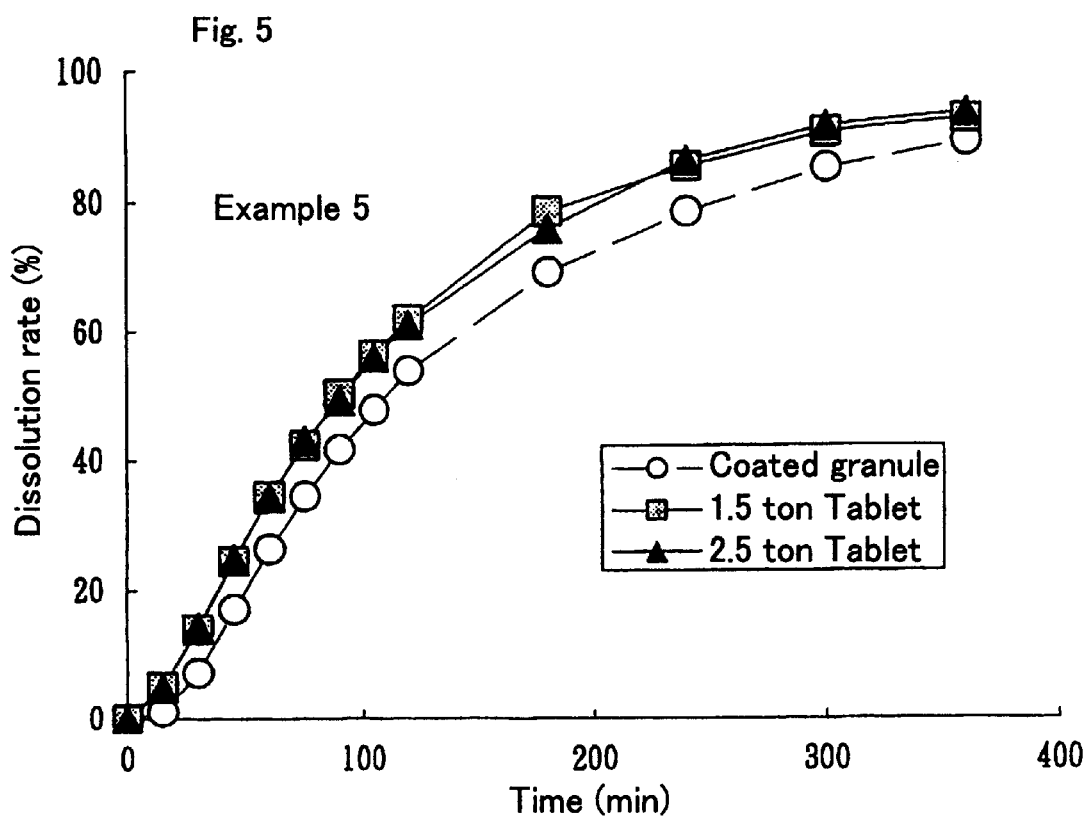
FIG. 5 shows the results from dissolution test of sustained release granules and tablets prepared in Example 5.
Figure 6:
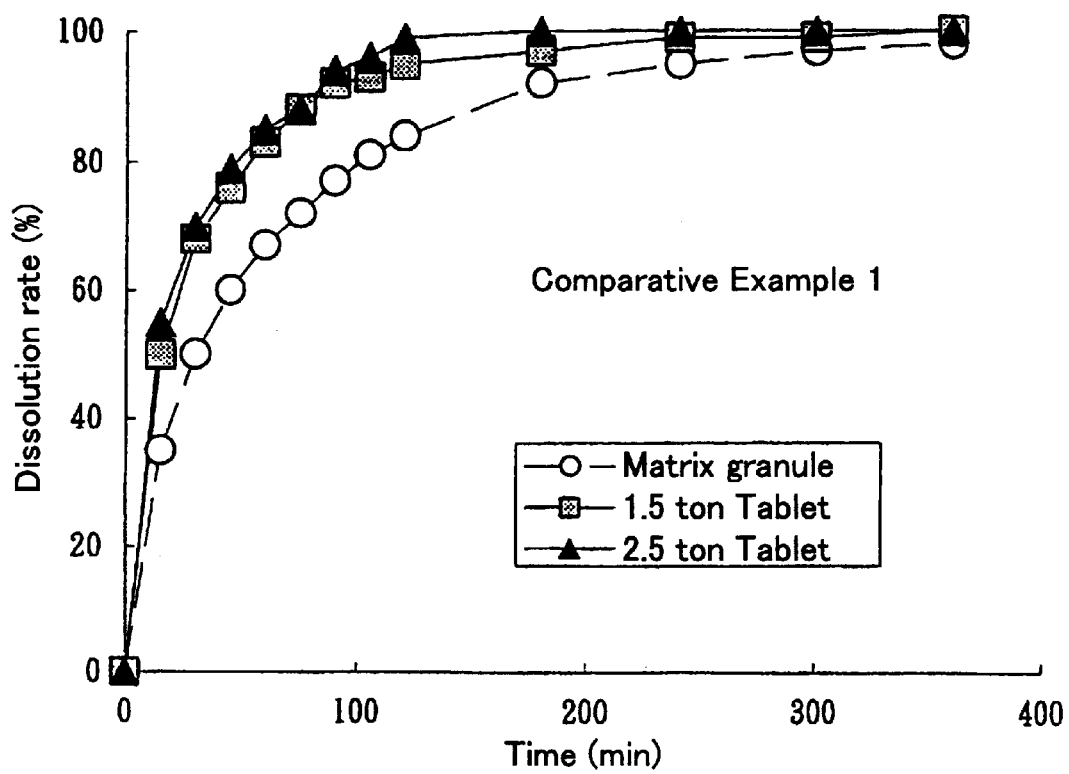
FIG. 6 shows the results from dissolution test of sustained release granules and tablets prepared in Comparative Example 1.
Figure 7:
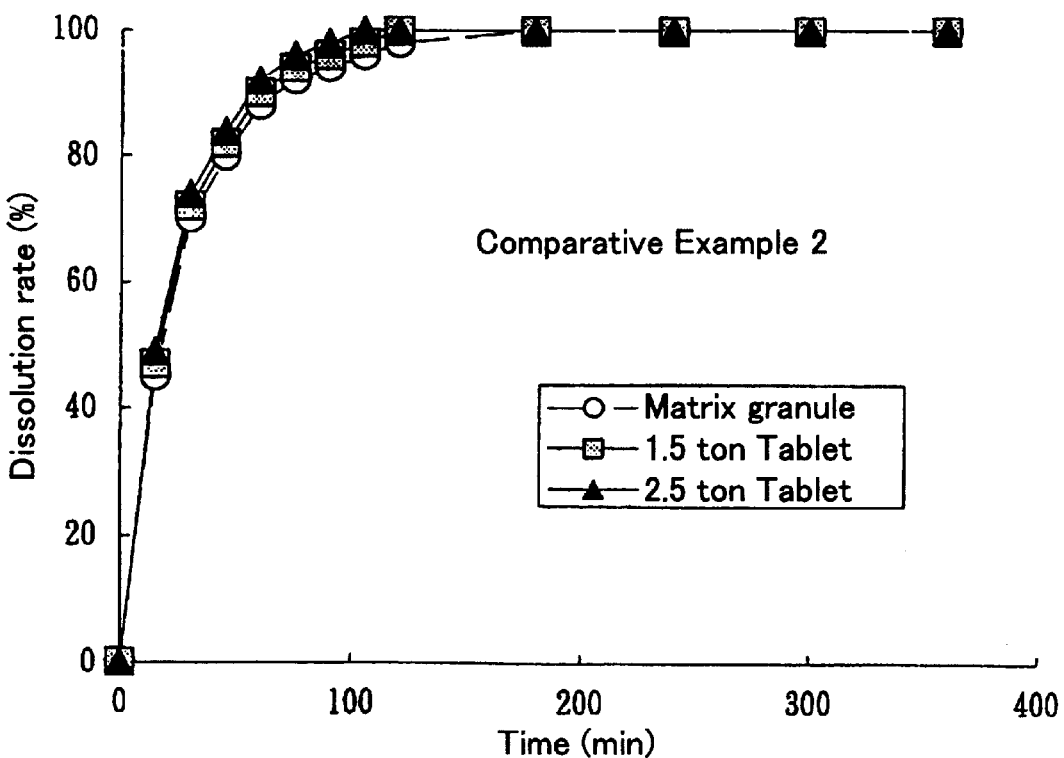
FIG. 7 shows the results from dissolution test of sustained release granules and tablets prepared in Comparative Example 2.
Figure 8:
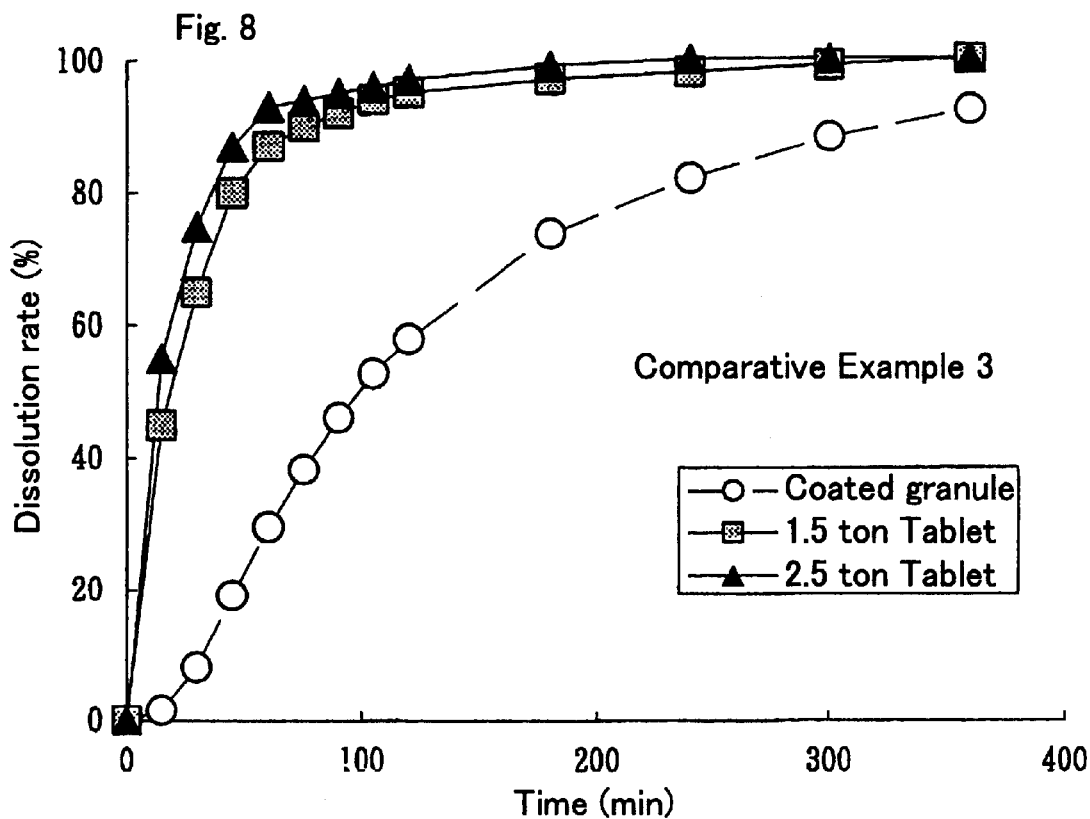
FIG. 8 shows the results from dissolution test of sustained release granules and tablets prepared by Comparative Example 3.
Figure 9:
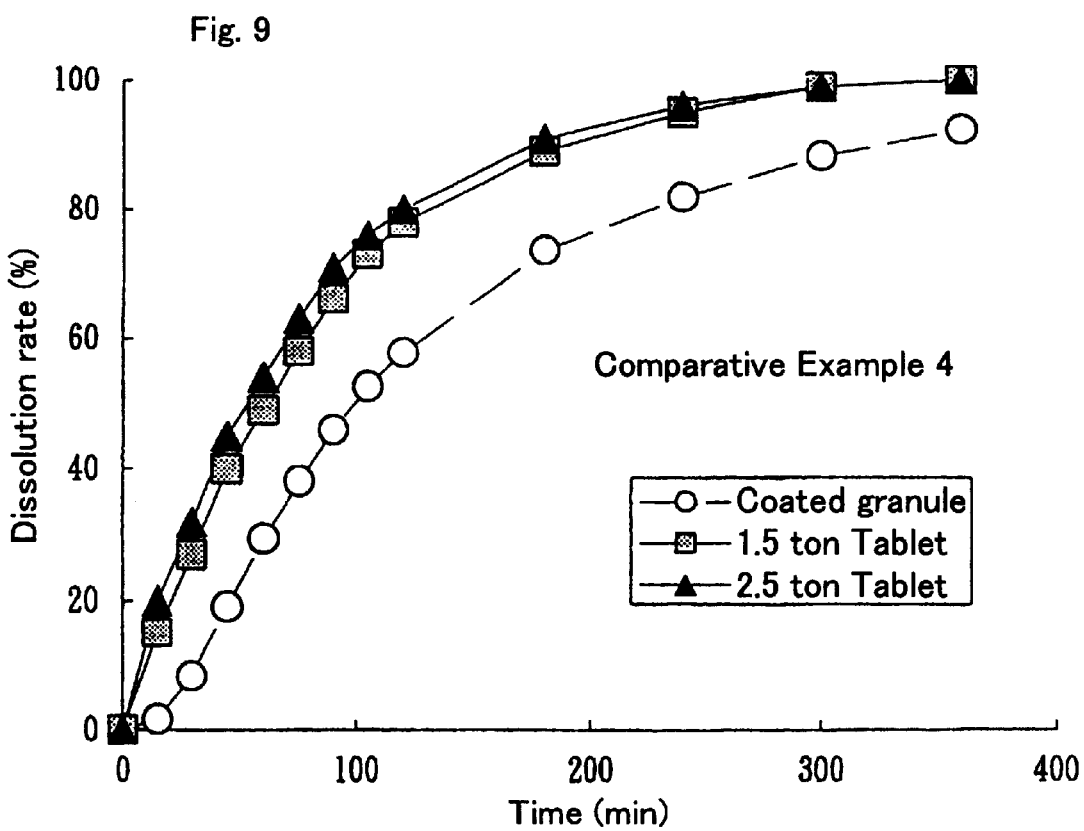
FIG. 9 shows the results from dissolution test of sustained release granules and tablets prepared in Comparative Example 4.
Figure 10:
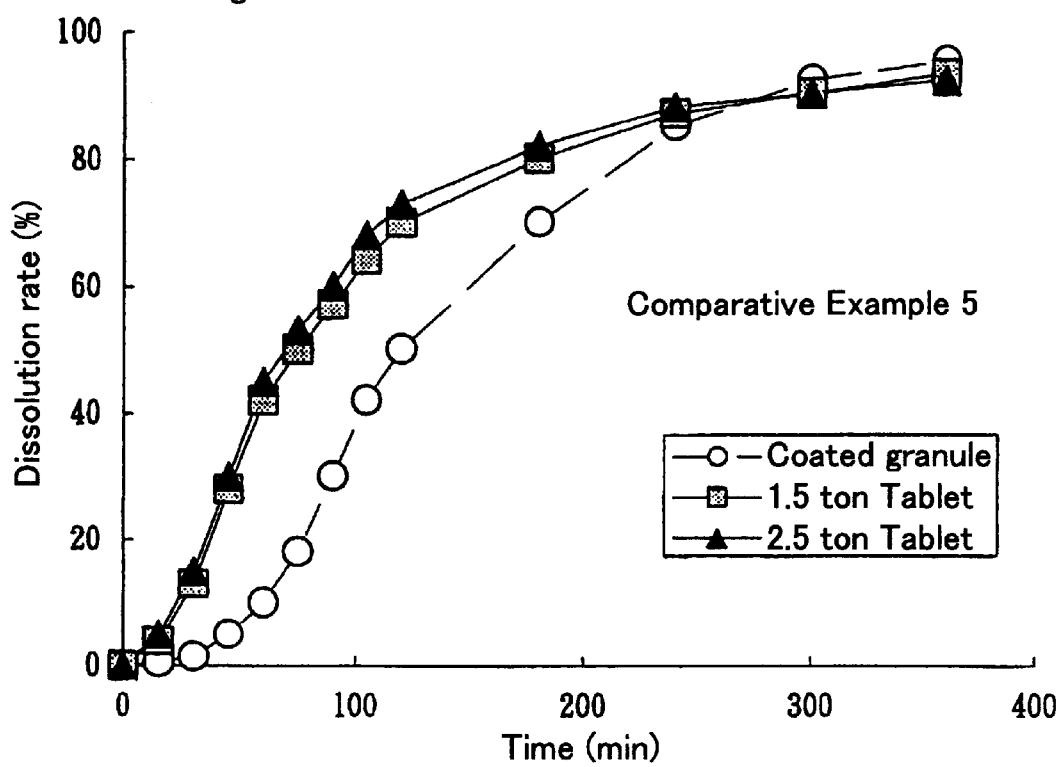
FIG. 10 shows the results from dissolution test of sustained release granules and tablets prepared in Comparative Example 5.

The test results are shown in FIGS. 1–10.

Test Example 2

The matrix granules (uncoated granules) prepared according to Examples 1–5 and Comparative Examples 1–5 were subjected to granule strength test. The test was carried out with a load cell of 2 kg and a compression speed of 0.10 $\mu$m/sec using GURANO granule strength tester (Okada Seiko Co., Ltd.). Granule strength was calculated according to the following equation, wherein the loaded weight at which granule was broken is defined as p (peak value):

(Granule strength)=2.8 p/(sectional area of granule)

The results are shown in Tables 3 and 4.

TABLE 3

[Results of strength test on granules of Examples 1–5 (uncoated granules)]

| | Example 1 | Example 2 | Example 3 | Example 4 | Example 5 |
|---|---|---|---|---|---|
| Granule strength (g/mm$^2$) | 3,500 | 3,800 | 3,800 | 3,650 | 3,300 |

TABLE 4

[Results of strength test on granules of
Comparative Examples 1–5 (uncoated granules)]

| | Comparative Example | | | | |
|---|---|---|---|---|---|
| | 1 | 2 | 3 | 4 | 5 |
| Granule strength (g/mm²) | 2,700 | 4,800 | 1,600 | 2,600 | 2,800 |

The above results reveal the following facts.

The matrix granule prepared using diprophylline as a model drug and Ethyl Cellulose-20 cps at a blending ratio of 1:1 could achieve 50% dissolution of the active ingredient in 100 minutes and showed little change in dissolution rate due to tableting (Example 1). On the other hand, the matrix granule prepared using diprophylline and Ethyl Cellulose-7 cps at a blending ratio of 1:1 provided 50% dissolution of the active ingredient in 30 minutes and showed increased dissolution rate due to tableting (Comparative Example 1). The shorter 50% dissolution time of the matrix granule of Comparative Example 1 compared with that of Example 1 is attributed to a lowered viscosity level 1% of ethyl cellulose from 20 cps to 7 cps. The increased dissolution rate due to tableting is attributed to the fact that granule strength of the matrix granule of Example 1 is 3,500 g/mm², while that of Comparative Example 1 is as low as 2,700 g/mm².

The matrix granule prepared using dextromethorphan hydrobromide as a model drug and Ethyl Cellulose-45 cps at a blending ratio of 1:1 could achieve 50% dissolution of the active ingredient in 60 minutes and showed little change in dissolution rate due to tableting (Example 2). Also, the 20 coated granule prepared by coating the above matrix granule with 15% Ethyl Cellulose-20 cps could achieve 50% dissolution of the active ingredient in 180 minutes and showed little change in dissolution rate due to tableting (Example 3).

The matrix granule prepared using phenylpropanolamine hydrochloride as a model drug and Ethyl Cellulose-45 cps at a blending ratio of 3:1 achieved 50% dissolution of the active ingredient in 20 minutes and a satisfactory sustained release could hardly be provided (Comparative Example 2). The coated granule prepared by coating the matrix granule, which had been prepared from Ethyl Cellulose-45 cps and the drug at a blending ratio of 1:1, with 20% Ethyl Cellulose-20 cps could achieve 50% dissolution of the active ingredient in 100 minutes and also showed little change in dissolution rate due to tableting (Example 4).

The uncoated granule was prepared using an ordinary binding agent (HPC-L) without using ethyl cellulose and then coated with Ethyl Cellulose-20 cps to form a coated granule. The coated granule showed 50% dissolution in 100 minutes, but showed considerably increased change in dissolution rate due to tableting (Comparative Example 3). The coated granules of Examples 3 and 4 showed little change Fin dissolution rate due to tableting, whereas the granule of Comparative Example 3 showed increased change. This is attributed to the facts that the granule strength of the former uncoated granules (matrix granules) is 3,800 g/mm² and 3,650 g/mm², respectively , while that of the latter is as low as 1,600 g/mm².

In the coated granule (Comparative Example 4), which was prepared in the same manner as described in Example 4 except that the ethyl cellulose used for the uncoated granule (matrix granule) was replaced by Ethyl Cellulose-7 cps, 50% dissolution time of the coated granule was almost the same with that of the coated granule of Example 4, but the more increased change in a dissolution rate due to tableting was shown as compared with that in Example 4. The reason for this may be that the granule strength of the sustained release granule of Comparative Example 4 is as low as 2,600 g/mm².

In the coated granule, which was prepared in the same manner as described in Example 3 except that a blending ratio of Ethyl Cellulose-45 cps to the drug for the uncoated granule (matrix granule) was changed to 0.75:1, little change in dissolution rate due to tableting was shown (Example 5). However, in the coated granule, which was prepared in the same manner as described in Example 3 except that a blending ratio of Ethyl Cellulose-45 cps to the drug for the uncoated granule (matrix granule) was changed to 0.5:1, somewhat increased change in dissolution rate due to tableting was shown (Comparative Example 5). The reason for this may be that the granule strength of the uncoated granule of Example 5 is relatively higher as 3,300 g/mm², while that of the uncoated granule of Comparative Example 5 is as low as 2,800 g/mm².

INDUSTRIAL APPLICABILITY

The multiple-unit sustained release tablet of the invention is different from the conventional granule in which the surface of an active ingredient is coated with a sustained release base, in that each granule comprises a matrix composed of a water-insoluble polymer and an active ingredient in admixture. This makes the granule of the invention hardly broken during mixing with the powdery part and compressing to tablets. Thus, dissolution rate changes little. Moreover, the coated granule prepared by coating the uncoated granule with a water-insoluble polymer, in which the uncoated granule has been made up as a hard matrix, can avoid the breakdown of the coating when compressed to tablets. Accordingly, the tablet of the present invention can provide a stable dissolution rate.

What is claimed is:

1. A multiple-unit sustained release tablet comprising a granular part and a powdery part, wherein each granule in the granular part comprises a matrix composed of a water-insoluble polymer and an active ingredient and wherein said granule has a granule strength of not less than 3,000 g/mm².

2. The multiple-unit sustained release tablet as claimed in claim 1, wherein said granule comprises a core particle and a matrix layer composed of a water-insoluble polymer and an active ingredient for coating said core particle.

3. The multiple-unit sustained release tablet as claimed in claim 1, wherein a weight ratio of said water-insoluble polymer to said active ingredient is 0.7:1–3:1.

4. The multiple-unit sustained release tablet as claimed in claim 1, wherein said water-insoluble polymer is ethyl cellulose.

5. The multiple-unit sustained release tablet as claimed in claim 4, wherein said ethyl cellulose has a viscosity of not less than 15 cps at 25° C. when dissolved at 5% by weight in a mixed solution of toluene and ethanol (8:2 w/w).

6. The multiple-unit sustained release tablet as claimed in claim 1, wherein said granule is coated with a release-controlling film.

7. The multiple-unit sustained release tablet as claimed in claim 6, wherein said release-controlling film is a water-insoluble polymer.

8. The multiple-unit sustained release tablet as claimed in claim 6, wherein said water-insoluble polymer is ethyl cellulose.

* * * * *